US006838270B1

(12) United States Patent
Kurosawa et al.

(10) Patent No.: US 6,838,270 B1
(45) Date of Patent: Jan. 4, 2005

(54) GENE ENCODING PROTEIN CAPABLE OF REGENERATING LUCIFERIN, NOVEL RECOMBINANT DNA, AND PROCESS FOR PRODUCING PROTEIN CAPABLE OF REGENERATING LUCIFERIN

(75) Inventors: Keiko Kurosawa, Chiba (JP); Naoki Kajiyama, Chiba (JP)

(73) Assignee: Kikkoman Corporation, Noda (JP)

( * ) Notice: Subject to any disclaimer, the term of this patent is extended or adjusted under 35 U.S.C. 154(b) by 154 days.

(21) Appl. No.: 10/089,986

(22) PCT Filed: Sep. 22, 2000

(86) PCT No.: PCT/JP00/06527

§ 371 (c)(1),
(2), (4) Date: Apr. 8, 2002

(87) PCT Pub. No.: WO01/25426

PCT Pub. Date: Apr. 12, 2001

(30) Foreign Application Priority Data

Oct. 6, 1999 (JP) .......................... 11/285258

(51) Int. Cl.[7] .............................. C12N 15/53; C12N 9/02
(52) U.S. Cl. ................... 435/189; 536/23.2; 435/320.1; 435/252.3; 435/325; 435/252.33
(58) Field of Search .............................. 435/189, 320.1, 435/252.3, 325, 252.33; 536/23.2

(56) References Cited

U.S. PATENT DOCUMENTS 5,814,504 A * 9/1998 Kajiyama ................... 435/189

FOREIGN PATENT DOCUMENTS

EP 825257 2/1998
WO 92/04468 3/1992

OTHER PUBLICATIONS

N. Shimokawa, et al., Federation of European Biochemical Societies, vol. 327, No. 3, XP–002227524, pp. 251–255, "Molecular Cloning and Sequencing of the cDNA Coding for a Calcium–Binding Protein Regucalcin from Rat Liver", Aug. 1993.
K. Okada, et al., Tetrahedron Letters, No. 32, XP–002109172, pp. 2771–2774, "Firefly Bioluminescence III. Conversion of Oxyluciferin to Luciferin in Firefly", 1974.
K. Gomi, et al., The Journal of Biological Chemistry, vol. 276, No. 39, XP–002227525, pp. 36508–36513, "Oxyluciferin, A Luminescence Product of Firefly Luciferase, is Enzymatically Regenerated into Luciferin", Sep. 28, 2001.
Anil Wipat et al., "The yvsA–yvqA region of the Bacillus subtilis chromosome containing genes involved in metal ion uptake and putative sigma factor", MICROBIOLOGY, vol. 144, pp. 1593–1600, (1998).

* cited by examiner

*Primary Examiner*—Rebecca E. Prouty
(74) *Attorney, Agent, or Firm*—Oblon, Spivak, McClelland, Maier & Neustadt, P.C.

(57) ABSTRACT

A gene encoding a protein which is capable of regenerating luciferin by acting on oxyluciferin and D-cysteine and thus regenerating luciferin; the above gene originating in a luminous organism; a protein encoded by the above gene; and a process for producing a protein capable of regenerating luciferin characterized by comprising culturing a transformant or a transductant having the above gene transferred therein and collecting the protein capable of regenerating luciferin from the culture. Thus, the protein capable of regenerating luciferin can be efficiently produced, which brings about a great industrial advantage.

9 Claims, No Drawings

SEQUENCE LISTING

<160> NUMBER OF SEQ ID NOS: 11

<210> SEQ ID NO 1
<211> LENGTH: 924
<212> TYPE: DNA
<213> ORGANISM: Photinus pyralis
<220> FEATURE:
<221> NAME/KEY: misc_feature
<222> LOCATION: (843)..(843)
<223> OTHER INFORMATION: n is a, g, t, or c

<400> SEQUENCE: 1

```
atggggccag ttgttgaaaa aattgcagaa cttggcaagt atacggttgg agaaggtcct    60
cactgggatc atgaaactca gaccttatat ttcgtcgaca ccgtagagaa aacttttcat   120
aaatatgtac cttctcagaa aaaatacacg ttttgtaaag tagataaact ggtttctttc   180
attattcccc ttgctggatc ccctggccgt tttgtagtca gtttggaacg tgaaatagcc   240
attcttacat gggatggcgt tagtgctgca cctacaagca tagaagctat tgttaatgtc   300
gaaccacaca ttaaaaataa cagactcaat gatggcaaag cagatcccct tggcaatcta   360
tggacaggta caatggctat tgacgctggt ctccccgtag accggtcac tggcagttta   420 tatcatttag ggctgataa aaaggtaaaa atgcacgaga gcaacatagc tatagcaaat   480
gggctcgcgt ggagtaatga tttgaagaaa atgtattata ttgattcggg gaaaagaaga   540
gtagacgagt acgattatga tgcttctaca ttatccatca gcaatcaacg gccattattt   600
acttttgaaa agcatgaagt gcctggatat ccagatggtc aaacaattga tgaggagggt   660
aatttatggg ttgccgtttt ccaaggacag cgaattatta aaatcagtac caacaaccg   720 gaagtgttac tggataccgt aaaaatacca gatcctcagg tcacctctgt agcatttggc   780
ggtccgaatt tggatgaact gcatgtaaca tctgctggtc ttcagcttga cgacagttct   840
ttngacaaaa gtttagttaa tgggcacgtc tacagagtaa caggtttagg cgtcaaaggt   900
ttcgcgggag ttaaagtgaa gcta                                         924
```

<210> SEQ ID NO 2
<211> LENGTH: 308
<212> TYPE: PRT
<213> ORGANISM: Photinus pyralis

<400> SEQUENCE: 2

```
Met Gly Pro Val Val Glu Lys Ile Ala Glu Leu Gly Lys Tyr Thr Val
 1               5                  10                  15

Gly Glu Gly Pro His Trp Asp His Glu Thr Gln Thr Leu Tyr Phe Val
            20                  25                  30

Asp Thr Val Glu Lys Thr Phe His Lys Tyr Val Pro Ser Gln Lys Lys
        35                  40                  45

Tyr Thr Phe Cys Lys Val Asp Lys Leu Val Ser Phe Ile Ile Pro Leu
    50                  55                  60
Ala Gly Ser Pro Gly Arg Phe Val Val Ser Leu Glu Arg Glu Ile Ala
65                  70                  75                  80

Ile Leu Thr Trp Asp Gly Val Ser Ala Ala Pro Thr Ser Ile Glu Ala
                85                  90                  95

Ile Val Asn Val Glu Pro His Ile Lys Asn Asn Arg Leu Asn Asp Gly
            100                 105                 110

Lys Ala Asp Pro Leu Gly Asn Leu Trp Thr Gly Thr Met Ala Ile Asp
        115                 120                 125
```

-continued

```
Ala Gly Leu Pro Val Gly Pro Val Thr Gly Ser Leu Tyr His Leu Gly
130                 135                 140

Ala Asp Lys Lys Val Lys Met His Glu Ser Asn Ile Ala Ile Ala Asn
145                 150                 155                 160

Gly Leu Ala Trp Ser Asn Asp Leu Lys Lys Met Tyr Tyr Ile Asp Ser
                165                 170                 175

Gly Lys Arg Arg Val Asp Glu Tyr Asp Tyr Asp Ala Ser Thr Leu Ser
            180                 185                 190

Ile Ser Asn Gln Arg Pro Leu Phe Thr Phe Glu Lys His Glu Val Pro
            195                 200                 205

Gly Tyr Pro Asp Gly Gln Thr Ile Asp Glu Glu Gly Asn Leu Trp Val
        210                 215                 220

Ala Val Phe Gln Gly Gln Arg Ile Ile Lys Ile Ser Thr Gln Gln Pro
225                 230                 235                 240

Glu Val Leu Leu Asp Thr Val Lys Ile Pro Asp Pro Gln Val Thr Ser
                245                 250                 255

Val Ala Phe Gly Gly Pro Asn Leu Asp Glu Leu His Val Thr Ser Ala
            260                 265                 270

Gly Leu Gln Leu Asp Asp Ser Ser Leu Asp Lys Ser Leu Val Asn Gly
        275                 280                 285

His Val Tyr Arg Val Thr Gly Leu Gly Val Lys Gly Phe Ala Gly Val
    290                 295                 300

Lys Val Lys Leu
305
```

<210> SEQ ID NO 3
<211> LENGTH: 24
<212> TYPE: DNA
<213> ORGANISM: Artificial Sequence
<220> FEATURE:
<223> OTHER INFORMATION: synthetic DNA

<400> SEQUENCE: 3
gttggagaag gaccgatttg ggat                                      24

<210> SEQ ID NO 4
<211> LENGTH: 29
<212> TYPE: DNA
<213> ORGANISM: Artificial Sequence
<220> FEATURE:
<223> OTHER INFORMATION: synthetic DNA

<400> SEQUENCE: 4
tcatccaagt tggggccgcc aaacgcgac                                 29

<210> SEQ ID NO 5
<211> LENGTH: 20
<212> TYPE: DNA
<213> ORGANISM: Artificial Sequence
<220> FEATURE:
<223> OTHER INFORMATION: synthetic DNA

<400> SEQUENCE: 5
ggacaggtac aatggctatt                                           20

<210> SEQ ID NO 6
<211> LENGTH: 20
<212> TYPE: DNA
<213> ORGANISM: Artificial Sequence
<220> FEATURE:
<223> OTHER INFORMATION: synthetic DNA

```
<400> SEQUENCE: 6
atcgtactcg tctactcttc                                                    20

<210> SEQ ID NO 7
<211> LENGTH: 22
<212> TYPE: DNA
<213> ORGANISM: Artificial Sequence
<220> FEATURE:
<223> OTHER INFORMATION: synthetic DNA

<400> SEQUENCE: 7
taggtgcagc actaacgcca tc                                                 22

<210> SEQ ID NO 8
<211> LENGTH: 21
<212> TYPE: DNA
<213> ORGANISM: Artificial Sequence
<220> FEATURE:
<223> OTHER INFORMATION: synthetic DNA

<400> SEQUENCE: 8
ttcacgttcc aaactgacta c                                                  21

<210> SEQ ID NO 9
<211> LENGTH: 23
<212> TYPE: DNA
<213> ORGANISM: Artificial Sequence
<220> FEATURE:
<223> OTHER INFORMATION: synthetic DNA

<400> SEQUENCE: 9
ctcgcgtgga gtaatgattt gaa                                                23

<210> SEQ ID NO 10
<211> LENGTH: 33
<212> TYPE: DNA
<213> ORGANISM: Artificial Sequence
<220> FEATURE:
<223> OTHER INFORMATION: synthetic DNA

<400> SEQUENCE: 10
ggaattcatg gggccagttg ttgaaaaaat tgc                                     33

<210> SEQ ID NO 11
<211> LENGTH: 35
<212> TYPE: DNA
<213> ORGANISM: Artificial Sequence
<220> FEATURE:
<223> OTHER INFORMATION: synthetic DNA

<400> SEQUENCE: 11
aactgcagtc atagcttcac tttaactccc gcgaa                                   35
```

GENE ENCODING PROTEIN CAPABLE OF REGENERATING LUCIFERIN, NOVEL RECOMBINANT DNA, AND PROCESS FOR PRODUCING PROTEIN CAPABLE OF REGENERATING LUCIFERIN

TECHNICAL FIELD

The present invention relates to a gene encoding a protein capable of regenerating luciferin, a novel recombinant DNA, and process for producing a protein capable of regenerating luciferin.

BACKGROUND ART

Luciferin is a substrate of a bioluminescence enzyme, luciferase, and after emitting light as a result of luciferase reaction, is converted to oxyluciferin. ATP measurement methods using luciferase are widely used in the fields of medical science and food hygiene. However, luciferin which is used as a substrate, is expensive and the luciferase reaction is inhibited by oxyluciferin produced after reaction. Thus, removal of oxyluciferin or regeneration to luciferin will enable further development of the ATP measurement methods using luciferase. A protein which is derived from a firefly and capable of regenerating luciferin from oxyluciferin has been found (U.S. Pat. No. 5,814,504). However, only a small quantity of the protein can be extracted from a firefly body so that industrial application of the protein has been difficult.

Addition of such a protein capable of regenerating luciferin to the luciferin-luciferase reaction system enables improvement in durability of luminescence and reduction in the amount of luciferase and luciferin to be used.

DISCLOSURE OF THE INVENTION

The object of the present invention is to provide a process for producing a protein capable of regenerating luciferin using a recombinant DNA to which a gene encoding the protein capable of regenerating luciferin has been inserted.

As a result of dedicated research on the above object, we have succeeded in isolating a gene which is derived from an insect belonging to the class Coleoptera and encodes a protein capable of regenerating luciferin, determining the gene structure, and obtaining are combinant DNA by inserting a gene encoding a protein capable of regenerating luciferin into a vector DNA. Then we have completed the present invention by finding that a protein capable of regenerating luciferin can be produced efficiently by culturing a transformant or a transductant wherein the recombinant DNA is contained in a host cell.

That is, a first invention of the present invention is a gene which encodes a protein capable of regenerating luciferin by acting on oxyluciferin and D-cysteine.

A second invention of the present invention is the above gene which is derived from an organism capable of luminescence.

A third invention of the present invention is a gene which encodes the following protein (a) or (b):
(a) a protein which comprises an amino acid sequence represented by SEQ ID NO: 2;
(b) a protein which comprises an amino acid sequence derived from the amino acid sequence (a) by deletion, substitution, or addition of one or more amino acids, and is capable of regenerating luciferin.

A forth invention of the present invention is a gene which has 50% or more homology with the amino acid sequence represented by SEQ ID NO: 2 and encodes a protein capable of regenerating luciferin.

A fifth invention of the present invention is a novel recombinant DNA which is characterized in that the above gene encoding a protein capable of regenerating luciferin is inserted into vector DNA.

A sixth invention of the present invention is a transformant or a transductant which comprises the above recombinant DNA.

A seventh invention of the present invention is a process for producing a protein capable of regenerating luciferin which comprises culturing the above transformant or transductant in a medium and collecting the protein capable of regenerating luciferin from the culture product.

Hereinafter, the present invention is described in detail.

The gene of the present invention which encodes a protein capable of regenerating luciferin is obtained from a Coleoptera.

For example, the gene of the present invention which encodes a protein capable of regenerating luciferin can be obtained as follows.

First, mRNA is extracted from the luminous organ of an American firefly.

Next, synthetic DNA is prepared based on an amino acid sequence of a purified protein capable of regenerating luciferin and the codon frequency of an American firefly. Then a reverse transcription polymerase chain reaction (hereinafter abbreviated as a RT-PCR method) is performed using the mRNA obtained above as a template, thereby obtaining DNA encoding a part of the protein capable of regenerating luciferin.

cDNA is synthesized from the mRNA obtained above using reverse transcriptase. Then the cDNA, as an intact cDNA or as an amplified gene encoding a protein capable of regenerating luciferin by the PCR method, is incorporated into a vector DNA by standard techniques. Examples of a vector DNA used herein include a plasmid DNA, such as pUC19(Takara Shuzo), pBR322 (Takara Shuzo), pBluescript SK+ (Stratagene), and pMAL-C2 (NEW England Labs), and bacteriophage DNA, such as λ ENBL3 (Stratagene) and λ DASH II (Funakoshi). The obtained recombinant DNA is transformed or transduced into, for example, *Escherichia coli* K-12, preferably *Escherichia coli* JM109 (Toyobo), DH5α (Toyobo) or XL1-Blue (Funakoshi), thereby obtaining transformants or transductants, respectively. In addition to the above, examples of a host cell used herein include bacteria, such as *Escherichia coli* other than *E. coli* K-12, yeast, mold, Actinomycetes, silk worms, and animal cells.

Transformation can be performed by, for example D. M. Morrison's method (Method in Enzymology, 68, 326–331, 1979). Transduction can be performed by, for example B. Hohn's method (Method in Enzymology, 68, 299–309, 1979).

A novel recombinant DNA which is purified from the above transformant or transductant can be obtained by, for example, P. Guerry et al.'s method [J. Bacteriology, vol. 116, 1064–1066 (1973)] and D. B. Clewell's method [J. Bacteriology, vol. 110, 667–676 (1972)].

Further, the entire nucleotide sequence of a gene which encodes a protein capable of regenerating luciferin is analyzed (see SEQ ID NO: 1) using DNA comprising the above gene which encodes the protein capable of regenerating luciferin and a 373A DNA sequence system (Perkin-Elmer) indicated in the later described Example (9). Then, the primary sequence of amino acids of a polypeptide which is translated by a gene comprising the above nucleotide sequence is determined (see SEQ ID NO: 2).

Further, the present invention encompasses any gene which encodes a protein capable of regenerating luciferin comprising an amino acid sequence which is derived from the amino acid sequence of SEQ ID NO: 2 by deletion, substitution, or addition of one or more, preferably several amino acids and is capable of regenerating luciferin.

Furthermore, the present invention encompasses any gene which encodes a protein having a 50% or more homology with the amino acid sequence of SEQ ID NO: 2 and capable of regenerating luciferin.

Any method can be employed to obtain a gene which encodes a protein capable of regenerating luciferin comprising an amino acid sequence which is derived from the amino acid sequence of SEQ ID NO: 2 by deletion, substitution or addition of one or more amino acids and is capable of regenerating luciferin. Examples of such a method include site-directed mutagenesis which is a known technique to cause point mutation or deletion to occur in a gene, a method which involves selective cleavage of a gene, removal or addition of a selected nucleotide, and ligation of the gene, and an oligonucleotide mutation induction method.

A protein capable of regenerating luciferin can be produced as described below using a transformant or transductant capable of regenerating luciferin obtained as described above, for example, a strain belonging to the genus Escherichia. The above microorganism may be cultured by a normal solid culture method, preferably a liquid culture method.

A medium used for culturing the above microorganism is supplemented with, for example, one or more types of nitrogen source, such as yeast extract, Peptone, meat extract, corn steep liquor, or exudates of soybean or wheat koji; and one or more types of inorganic salt, such as potassium dihydrogenphosphate, dipotassium hydrogenphosphate, magnesium sulfate, ferric chloride, ferric sulfate or manganese sulfate, and if necessary, appropriately supplemented with carbohydrate material, vitamin and the like.

The initial pH of a medium is appropriately adjusted to 7 to 9. Culturing is performed at 30° C. to 42° C., preferably at around 37° C. for 6 to 24 hours by aeration (agitation)— submerged culture, shaking culture, stationary culture or the like. After culturing, a protein capable of regenerating luciferin can be collected from the culture product by normal techniques for collecting enzymes.

Cells were isolated from the culture product by a technique, such as filtration or centrifugation, and washed. The protein capable of regenerating luciferin is preferably collected from cells. In this case, intact cells can be used. Preferably, the protein capable of regenerating luciferin is collected from cells by, for example, a method which disrupts cells using various disruptive means, such as an ultrasonicator, french press or Dyno-Mill, a method which digests cell walls using a cell wall digesting enzyme, such as lysozyme, and a method which extracts enzyme from the cell using a surfactant, such as Triton X-100.

The protein capable of regenerating luciferin can be isolated from the thus obtained crude solution of protein having ability to regenerate luciferase by a standard technique for enzyme purification. Preferably performed is an appropriate combination of such techniques including ammonium sulfate salting out technique, precipitation technique using organic solvents, ion exchange chromatography, gel filtration chromatography, adsorption chromatography and electrophoresis.

The obtained protein capable of regenerating luciferin can regenerate luciferin by acting on oxyluciferin and D-cysteine.

(Method for Measuring Ability to Regenerate Luciferin)
(Reagent)
A 0.1 mM oxyluciferin
B 0.01 mM D-cysteine
C 25 mM glycylglycine+5.4 mM magnesium sulfate
D 10 mM ATP (pH7.8)
E 5 mg/ml luciferase
(Procedure)
1. Prepare a mixed solution of the following reagents.
   0. 005 ml A
   0. 010 ml B
   0. 085 ml C
2. Add 0.01 ml of the protein solution and allow to react at 37° C. for a certain time.
3. Mix 0.01 ml of the reaction solution with 0.1 ml of C.
4. Prepare a luciferase mixed solution of the following reagents.
   10 ml D
   1 ml E
5. Add 0.1 ml of the mixed solution of 4 to that of 3, and then measure the amount of light emitted using a luminometer.

BEST MODE FOR CARRYING OUT THE INVENTION

Hereinafter, the present invention is described in more detail by Examples.

EXAMPLES

Example 1

(1) Preparation of American firefly mRNA

The tail portion of American firefly (Sigma) 10 g disrupted with a mortar and a pestle was suspended in 10 ml of ISOGEN (Wako Pure Chemical Industries, Ltd.), a reagent for extracting RNA, and then centrifuged at 2700 r.p.m. for 5 min, thereby obtaining RNA fraction. From the fraction, 0.51 mg of mRNA was obtained according to the method described in the Current Protocols in Molecular Biology (WILEY Interscience, 1989).

(2) Synthesis of Primer

Approximately 10 $\mu$g of the protein capable of regenerating luciferin purified in (1) was subjected to a protein sequencer (Perkin-Elmer Corporation), so that the N-terminal amino acid sequence was determined. Further, approximately 10 $\mu$g of the protein capable of regenerating luciferin purified in (1) was digested with trypsin. Then 6 peptides obtained with HPLC were subjected to a protein sequencer, so that the internal amino acid sequence was determined. Furthermore, the codon frequency of American firefly was examined. Based on this information, primers shown in SEQ ID NOS: 3 and 4 were synthesized by Amersham Pharmacia Biotech's entrusted custom synthesis.

(3) RT-PCR

A reaction solution was prepared to have the following composition, and a reverse transcription reaction was allowed to proceed for 30 min at 42° C. Then, denaturation was performed at 99° C. for 5 min, and then stored at 5° C.

(Composition of Reaction Solution)

| | |
|---|---|
| Magnesium chloride | 5 mM |
| *10xRNA PCR buffer | 2 $\mu$l |
| water | 8.5 $\mu$l |
| dNTP | 1 mM each |

-continued

| RNase inhibitor | 1 U/µl |
| *AMV reverse transcriptase XL | 0.25 U/µl |
| *oligo dT adapter primer | 0.125 µM |
| mRNA | 1 µg |

*manufactured by Takara Shuzo

Next, 80 µl of the reaction solution prepared to have the following composition was added to a tube in which reverse transcription had been performed. Then PCR was performed under a reaction condition for 30 cycles, each consisting of denaturation at 94° C. for 30 sec, annealing at 62° C. for 30 sec, and elongation reaction at 72° C. for 1.5 min.

(Composition of Reaction Solution)

| Primer (SEQ ID NO: 3) | 0.2 µM |
| Primer (SEQ ID NO: 4) | 0.2 µM |
| *10xRNA PCR buffer | 8 µl |
| Magnesium chloride | 2.5 mM |
| *Taq polymerase | 2.5 Unit |
| Water (add water to a final volume of 80 µl) | |

*manufactured by Takara Shuzo

After PCR, the reaction solution was subjected to agarose gel electrophoresis, so that a band of approximately 0.75 kb regarded as a target fragment was confirmed. The band was cut out and purified with GENECLEAN II (BIO 101).

(4) Determination and Analysis of Nucleotide Sequence of Purified DNA Fragment

The nucleotide sequence of the purified DNA fragment was determined and analyzed using a 373A DNA sequence system (Perkin-Elmer). Thus, an amino acid sequence which had been deduced from the determined nucleotide sequence was confirmed to comprise the previously described amino acid sequence (His Glu Thr Gln Thr Leu Tyr Phe Val Asp Thr) (SEQ ID NO: 2 rues 24–34). Thus, a partial sequence of the gene which encodes a protein capable of regenerating luciferin was confirmed to be present in the DNA fragment amplified by the above RT-PCR.

(5) Analysis of Downstream Region by 3'RACE

First, a primer was designed according to the above analysis for DNA sequence, and then synthesized by Amersham Pharmacia Biotech (SEQ ID NO: 5). RT-PCR was performed using the primer, the above mRNA and 3'-Full RACE CoreSet (Takara Shuzo), thereby amplifying 3' unknown region. The reaction solution was subjected to agarose electrophoresis, a DNA fragment of approximately 650 bp was purified and extracted with RecoChip (Takara Shuzo), and the nucleotide sequence was determined and analyzed using a DNA sequencer. Therefore, the 5' region of the determined nucleotide sequence was confirmed to contain a sequence being the same as that of the 3' sequence of the partial sequence of the above gene encoding a protein capable of regenerating luciferin. Further, an amino acid sequence which had been deduced from the determined nucleotide sequence was confirmed to comprise the previously described amino acid sequence (Ile Pro Asp Pro Gln Val Thr Ser Val Ala Phe Gly Gly Pro Asn Leu Asp Glu)(SEQ ID NO: 2 residues 249–266).

(6) Analysis of Upstream Region by 5' RACE

First, primers were designed according to the above analysis for DNA sequence, and then synthesized by Amersham Pharmacia Biotech (SEQ ID NOS: 6 to 9). RT-PCR was performed using the primers, the above mRNA and 5'-Full RACE CoreSet (Takara Shuzo), thereby amplifying 5' unknown region. The reaction solution was subjected to agarose electrophoresis, a DNA fragment of approximately 400 bp was purified and extracted with RecoChip (Takara Shuzo), and the nucleotide sequence was determined and analyzed using a DNA sequencer. Therefore, the determined nucleotide sequence was confirmed to contain a sequence being the same as that of the partial sequence of the above gene encoding a protein capable of regenerating luciferin. Further, an amino acid sequence which had been deduced from the determined nucleotide sequence was confirmed to comprise the previously described amino acid sequence (Gly Pro Val Val Glu Lys Ile Ala Glu Leu Gly Lys)(SEQ ID NO: 2 residues 2–3).

(7) Recovery of Gene Fragment by RT-PCR

A translation initiation codon and a termination codon were deduced from the above three nucleotide sequences, and then the primer DNAs of the N terminal region and the C terminal region were synthesized by Amersham Pharmacia Biotech (SEQ ID NOS: 10 and 11). RT-PCR was performed using the primers and the above mRNA, and then the reaction solution was analyzed by agarose electrophoresis. As a result, a band of approximately 900 bp was confirmed. A DNA fragment contained in the band was purified and extracted with a RecoChip (Takara Shuzo), followed by digestion with restriction enzymes EcoRI and PstI (both manufactured by Takara Shuzo). Separately, a plasmid pKK223-3 (Pharmacia) was digested with restriction enzymes EcoRI and PstI and purified by agarose electrophoresis. This was ligated to the above purified and extracted DNA fragment, and then transformation of E. coli JM109 (Toyobo) was performed. The transformant strain, E. coli JM109 (pLRE), was deposited to Patent and Bio-Resource Center, National Institute of Advanced Industrial Science and Technology as FERM BP-6908.

(8) Confirmation of Activity

E. coli JM109 (pLRE) cells were shake-cultured to Klett 100at 37° C. in 10 ml of TY medium (1% bacto trypton, 0.5% bactoyeast extract, 0.5% NaCl, pH 7.0) containing 50 µg/ml ampicillin. Then, IPTG was added to a final concentration of 1 mM, followed by another 4 hours of culturing. The culture solution was treated 4 times (20 sec each) using an ultrasonicator (Ultrasonicgenerator, Nissei) while cooling on ice. The solution was put into an Eppendorf tube, and centrifuged at 12,000 r.p.m. with a micro centrifuge for 10 min, thereby separating into supernatant and precipitation fractions. The supernatant was transferred to another Eppendorf tube and ability thereof to regenerate luciferin was measured by the previously described method for measuring enzyme activity. While E. coli comprising only a vector had 0.94 kcount/ml, E. coli JM109 (pLRE) had 10.58 kcount/ml and was confirmed to be capable of regenerating luciferin.

(9) Analysis of Gene Encoding Protein Capable of Regenerating Luciferin

Confirmation of the luciferin regenerating ability of E. coli JM109 (pLRE) revealed that the insertion fragment of pLRE comprised the gene of the protein capable of regenerating luciferin. Then, the nucleotide sequence was determined for the plasmid DNA using a 373A DNA sequence system (Perkin-Elmer). The determined nucleotide sequence and an amino acid sequence of a polypeptide which is translated from the DNA sequence are shown in SEQ ID NO: 1 and SEQ ID NO: 2, respectively. The gene of the protein capable of regenerating luciferin had a coding region of 924 bp and encoded 308 amino acids.

INDUSTRIAL APPLICABILITY

The invention is industrially very useful because the invention enables efficient production of a protein capable of regenerating luciferin.

What is claimed is:

1. An isolated polynucleotide encoding a protein comprising the amino acid sequence of SEQ ID NO: 2 or a fragment thereof,
   wherein said protein or protein fragment regenerates luciferin.

2. The isolated polynucleotide of claim 1, which encodes a polypeptide comprising SEQ ID NO: 2.

3. The isolated polynucleotide of claim 1, which encodes a polypeptide which comprises a fragment of SEQ ID NO: 2.

4. A vector comprising the isolated polynucleotide of claim 1.

5. A host cell comprising the isolated polynucleotide of claim 1.

6. A method of producing a protein that can regenerate luciferin comprising:

culturing the host cell of claim 5 in a medium, and collecting the protein.

7. The method of claim 6, further comprising isolating or purifying said protein.

8. The method of claim 6, comprising culturing *Escherichia coli* JM109 (pLRE).

9. *Escherichia coli* JM109 (pLRE) (FERM BP-6908).

* * * * *